US007066172B2

(12) United States Patent
Pasternack

(10) Patent No.: US 7,066,172 B2
(45) Date of Patent: Jun. 27, 2006

(54) WARNING DEVICE FOR A RESPIRATOR PRODUCT

(75) Inventor: Adalbert Pasternack, Bad Schwartau (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 249 days.

(21) Appl. No.: 10/449,464

(22) Filed: May 29, 2003

(65) Prior Publication Data

US 2004/0050388 A1 Mar. 18, 2004

(30) Foreign Application Priority Data

Sep. 17, 2002 (DE) ................................ 102 43 001

(51) Int. Cl.
*A61M 16/00* (2006.01)

(52) U.S. Cl. ........................... 128/202.22; 128/205.22; 128/205.23

(58) Field of Classification Search ........... 128/200.24, 128/201.25, 202.22, 205.22, 205.23
See application file for complete search history.

(56) References Cited

U.S. PATENT DOCUMENTS 2,299,793 A * 10/1942 Cannaday et al. ..... 128/202.13
2,490,839 A * 12/1949 Shaffer et al. ................ 48/190
2,894,478 A * 7/1959 Reed et al. ................. 116/214
2,989,294 A * 6/1961 Coker ........................... 299/2
3,861,350 A * 1/1975 Selleck ........................ 116/214
3,911,413 A * 10/1975 Wallace ....................... 340/632
4,165,738 A * 8/1979 Graves et al. ......... 128/202.13
4,413,622 A * 11/1983 Austin ................... 128/205.25
4,510,930 A * 4/1985 Garcia ................... 128/202.22
4,862,931 A * 9/1989 Vella ............................. 141/1
5,055,822 A * 10/1991 Campbell et al. ........ 340/407.1
5,552,088 A * 9/1996 Pottier et al. ............... 116/214
5,666,949 A * 9/1997 Debe et al. ............ 128/202.22
2003/0105407 A1 6/2003 Pearce, Jr. et al.

FOREIGN PATENT DOCUMENTS

| | | |
|---|---|---|
| DE | 155348 | 8/1938 |
| DE | AS 11 29 376 | 5/1962 |
| DE | 197 53 956 | 6/1999 |
| GB | 287562 | 10/1928 |
| GB | 462514 | 3/1937 |

* cited by examiner

*Primary Examiner*—Aaron J. Lewis
(74) *Attorney, Agent, or Firm*—McGlew & Tuttle, P.C.

(57) ABSTRACT

A warning device for a respirator product with a valve (11), which comes into action in a state of warning and releases a gas flow. The warning does not hinder the user of the apparatus and only a very small portion of the gas supply carried with the user is used by the warning device. The gas flow is brought into the range of perception of a person via a scent cartridge (9).

10 Claims, 1 Drawing Sheet

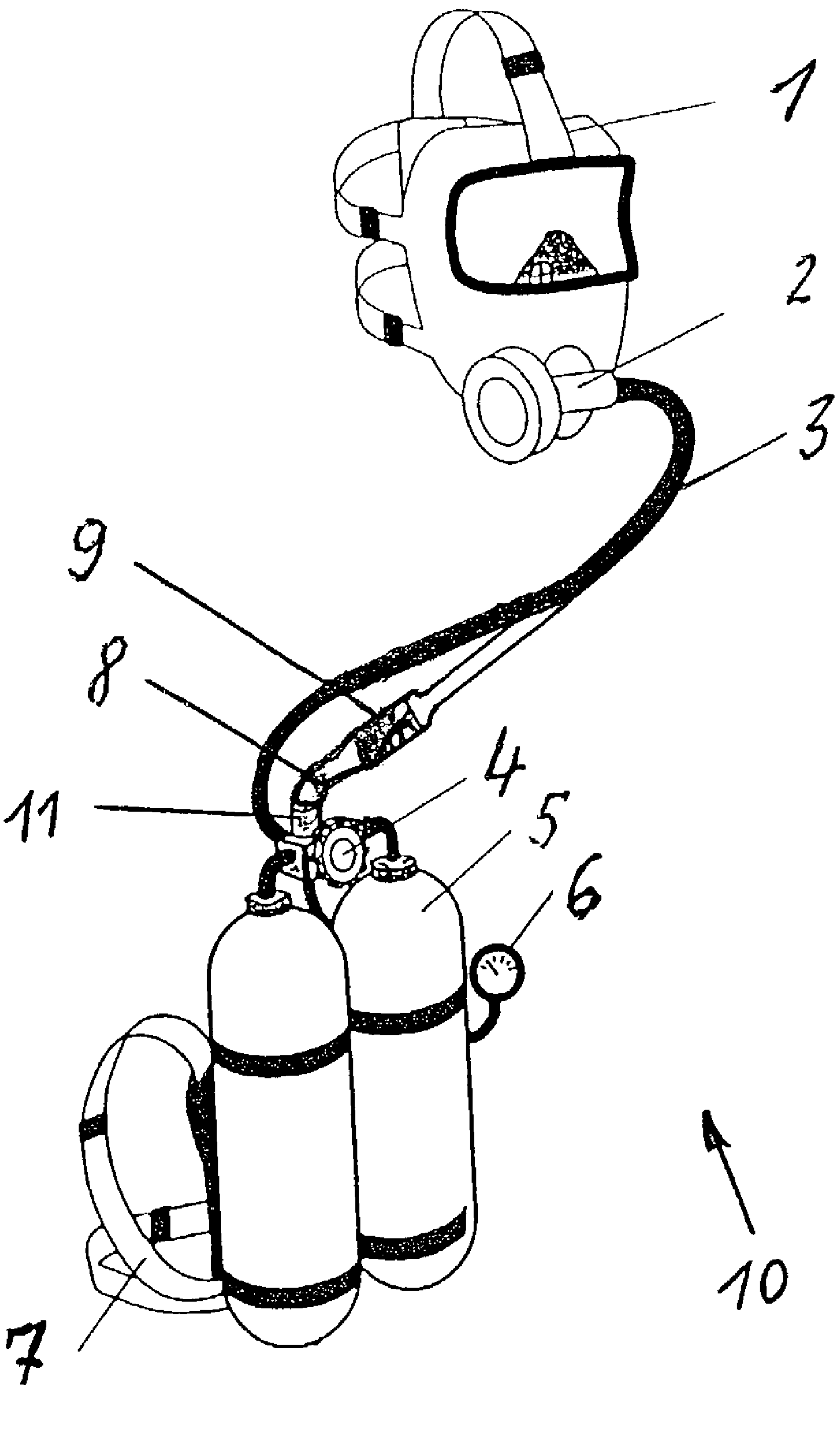
1
2
3
9
8
4
11
5
6
10
7

WARNING DEVICE FOR A RESPIRATOR PRODUCT

FIELD OF THE INVENTION

Respirator products protect the user of the device from the inhalation of hazardous substances and supply the oxygen needed for the breathing. The duration of protection ensured by compressed air breathing apparatuses depends on the amount of breathing air reserve carried with the apparatus. The depletion of the reserve must be indicated to the user of the apparatus to ensure that a sufficient breathing gas volume is still present for retreat. A warning signal is triggered for this purpose when a certain warning pressure is reached in the compressed gas reservoir.

BACKGROUND OF THE INVENTION

A respirator with a compressed gas reservoir and a warning device, which sends an acoustic signal in the form of a whistling sound when a warning pressure is reached, has become known from DE-AS 11 29 376. A lung-controlled valve located on a breathing mask is connected to two compressed gas sources via a connection piece. One of the compressed gas sources is fastened on the back of the user of the apparatus. The other compressed gas source is arranged stationarily away from the user of the apparatus, and the compressed gas is fed to the lung-controlled valve via a flexible supply tube. In the normal case, the user of the apparatus receives his breathing gas via the flexible supply tube from the stationary compressed gas source. When the supply pressure drops below a certain value, a changeover is performed by means of a pressure-actuated changeover switch to the compressed gas cylinder located at the user of the apparatus, and a partial flow, which reaches an acoustic signal device, is branched off at the same time from the gas flow sent to the lung-controlled valve.

The drawback of the prior-art device is that the acoustic signal is felt by the user of the apparatus to be disturbing, and the gas flow flowing through the signal device additionally consumes some of the gas present in the breathing gas reservoir. In addition, an acoustic signal is not always perceptible in case of louder ambient noise.

Warning devices in which the inspiration resistance is increased have been known as well. Their drawback is that the user of the apparatus does not receive a sufficient amount of air any longer and may panic.

Electronic warning devices require a considerable design effort due to the compliance with the explosion protection regulations.

SUMMARY OF THE INVENTION

The basic object of the present invention is to improve a warning device for a respirator product such that the user of the apparatus is not hindered and the gas reserve carried with him is not used to an appreciable extent. The object is, furthermore, to provide a process for indicating a state of warning.

According to the invention, a warning device for a respirator product is provided with a valve, which comes into action in a state of warning and releases a gas flow. The gas flow released by the valve is brought into the range of perception of a person via a scent cartridge.

According to another aspect of the invention, a process is provided for indicating a state of warning in a respirator product. The respirator product has a valve, which releases a gas flow in the case of warning. The process includes the steps of sending the gas flow via a scent cartridge into the range of perception of a person.

According to another aspect of the invention, a respirator system is provided with a pressurized gas source, a breathing air supply line, a user connection providing breathing air to a user with the user connection being connected to the supply line. The system has a pressure reducer provided between the pressurized gas source and the user connection. The system has a warning device with scent means for adding scent to the breathing air in the supply line upon the occurrence of a predetermined state.

The warning device with scent means includes a valve which comes into action in a state of warning and releases a gas flow into the supply line. This is preferably a pressure responsive valve, responsive to the pressure level of the pressurized gas source falling below some predefined threshold. A scent cartridge is operatively connected to the released gas flow for influencing the scent of the gas flow to bring the warning into the range of perception of a user via the scent. The warning device with scent means may include a flexible gas supply tube connecting the valve and the scent cartridge to the supply line so the gas flow discharged from the scent cartridge is introduced into the flexible gas supply tube leading to the breathing mask.

The pressurized gas source is advantageously one or more gas cylinders, preferably a set that can be strapped on the back of the user. The user connection includes a breathing mask and a lung-controlled valve connected to the supply line.

The advantage of the present invention is essentially that the gas flow released in the case of warning reaches the range of perception, i.e., the nose of the user of the apparatus, via a scent cartridge. Since the human nose is able to perceive very low scent concentrations, only a a very small gas flow must be sent over the scent cartridge. The compressed gas reserve carried by the user is hardly burdened by the small gas flow, and, moreover, the scent cartridge has a long service life.

The gas flow discharged from the scent cartridge may be introduced into a flexible gas supply tube leading to a breathing mask.

The process may also include introducing the gas flow being discharged from the scent cartridge into the flexible gas supply tube leading to the breathing mask. The scent cartridge, through which gas flows in the case of warning may be used as a warning device for respiration protection or in respiration protection systems.

It is especially advantageous for the gas flow being discharged from the scent cartridge to be introduced into the flexible gas supply tube leading to the lung-controlled valve. There is no loss of breathing gas because the gas flow leaving via the scent cartridge is returned.

The present invention is not limited to the indication of an imminent shortage of gas, but the valve, which releases the gas flow via the scent cartridge, may also be actuated by a gas measuring device, which monitors the concentration of hazardous substances in the environment and sends, e.g., a control signal to the valve in case of an explosion hazard. A plurality of scent cartridges may also be present, which are activated in different states of warning.

An advantageous use of a scent cartridge in respirator systems and respirator devices is to send a gas flow via the scent cartridge in case of warning such that the gas enriched with the scent can be perceived by the user of the respirator.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

The only FIGURE is a perspective view of the device and system according to the invention.

DESCRIPTION OF THE PREFERRED EMBODIMENT

Referring to the drawings in particular, the only FIGURE schematically shows a compressed air breathing apparatus 10, in which the breathing air flows from two compressed gas cylinders 5 into a breathing mask 1 via a pressure reducer 4, a flexible gas supply tube 3 and a lung-controlled valve 2. The pressure reducer 4 reduces the cylinder pressure to the so-called center pressure. The compressed gas cylinders 5 are fastened on the back of a user of the apparatus, not shown specifically in the figure, by means of straps 7. The pressure prevailing in the compressed gas cylinders 5 can be read on the pressure gauge 6.

If the pressure in the compressed gas cylinders 5 reaches a warning pressure of 50 bar, a small gas flow is sent via a line 8 into the scent cartridge 9 via a valve 11 at the pressure reducer 4. Odoriferous substances, which are fed into the flexible gas supply tube 3, are released during the flow through the scent cartridge 9. The user of the apparatus is thus warned of the compressed gas reserve becoming depleted, and he can begin to retreat from the environment for which the respiration system is needed.

The system according to the invention includes a pressurized gas source in the form of the gas cylinders 5 as well as the breathing mask 1, the pressure reducer 4, a breathing air supply line in the form of the flexible gas supply tube 3 and the lung-controlled valve 2. The pressure responsive valve 11, the line 8 and the sent cartridge 9 form a warning means for warning the user of some status change, such as the compressed gas cylinders 5 reaching the warning pressure (e.g., 50 bar).

While specific embodiments of the invention have been shown and described in detail to illustrate the application of the principles of the invention, it will be understood that the invention may be embodied otherwise without departing from such principles.

What is claimed is:

1. A warning device for a respirator product with a breathing air supply line, the device comprising:

scent means for adding scent to the breathing air in the supply line upon the occurrence of a predetermined state, said sent means includes a scent gas flow line connected to the supply line, a valve which comes into action in a state of warming and releases a breathing gas flow into said scent gas line and via the scent gas line to the supply line and a scent cartridge operatively connected to the scent gas line for influencing the scent of the breathing gas flow in the scent gas line and thereby for influencing the scent of breathing air in the supply line to bring the warning into the range of perception of a person via the scent.

2. A warning device in accordance with claim 1, wherein the respirator product includes a breathing mask connected to the supply line and the supply line is a flexible gas supply tube wherein the gas flow discharged from the scent gas line operatively connected to said scent cartridge is introduced into said flexible gas supply tube leading to the breathing mask.

3. A process for indicating a state of warning in a respirator product, wherein the respirator product has a valve, the process comprising the steps of:

providing a pressurized breathing gas source and a breathing gas supply line connected to the breathing gas source and leading to a user breathing connection;

providing a scent gas line connected to the pressurized gas source via the valve and connected to the supply line;

operatively connecting a scent cartridge to the scent gas line;

releasing a gas flow in the case of a warning into the scent gas line for sending the released gas flow via the scent gas line and connected scent cartridge into the breathing gas supply line and thereby via the user breathing connection into the range of perception of a user connected to the respirator product via the user breathing connection.

4. A process in accordance with claim 3, wherein the breathing gas supply line is a flexible gas supply line and the user breathing connection is a breathing mask and the gas flow being discharged from the scent gas line, with operatively connected scent cartridge, is introduced into the flexible gas supply tube leading to the breathing mask.

5. A process according to claim 4, wherein the mask is part of a respiration system with the scent cartridge used as part of a warning device for respiration protection.

6. A process according to claim 4, further comprising the step of:

providing a pressure reducer between the pressurized gas source and the breathing mask.

7. A process according to claim 3, further comprising providing a pressure reducer between the pressurized breathing gas source and the user breathing connection.

8. A respirator system, comprising:

a pressurized gas source;

a breathing air supply line;

a user connection providing breathing air to a user, the user connection being connected to the supply line;

a pressure reducer provided between the pressurized gas source and the user connection; and a warning device comprising a scent gas line connected at a discharge end to said breathing air supply line, a valve connected to said pressurized gas source and connected to said scent gas line, sad valve releasing a gas flow into said supply line via said gas scent line, and a scent cartridge operatively connected to said scent gas line for influencing the scent of the gas flow released by said valve for adding scent to the breathing air in the supply line upon the occurrence of a predetermined state.

9. A respirator system according to claim 8, wherein said pressurized gas source comprises one or more gas cylinders and said user connection includes a breathing mask and a lung-controlled valve connected to said supply line.

10. A warning device in accordance with claim 9, wherein said supply line is a flexible gas supply tube wherein the gas flow discharged from the scent cartridge is introduced into said flexible gas supply tube leading to said breathing mask.

* * * * *